US011835509B2

(12) United States Patent
Ioka

(10) Patent No.: US 11,835,509 B2
(45) Date of Patent: Dec. 5, 2023

(54) SPECIMEN ANALYSIS APPARATUS, SPECIMEN ANALYSIS METHOD, AND COMPUTER-READABLE RECORDING MEDIUM

(71) Applicant: EVIDENT CORPORATION, Nagano (JP)

(72) Inventor: Ken Ioka, Hachioji (JP)

(73) Assignee: Evident Corporation, Nagano (JP)

( * ) Notice: Subject to any disclaimer, the term of this patent is extended or adjusted under 35 U.S.C. 154(b) by 652 days.

(21) Appl. No.: 17/069,032

(22) Filed: Oct. 13, 2020

(65) Prior Publication Data
US 2021/0027464 A1 Jan. 28, 2021

Related U.S. Application Data

(63) Continuation of application No. PCT/JP2018/015764, filed on Apr. 16, 2018.

(51) Int. Cl.
*G06V 10/56* (2022.01)
*G01N 33/483* (2006.01)
(Continued)

(52) U.S. Cl.
CPC ..... *G01N 33/4833* (2013.01); *G01N 15/1468* (2013.01); *G06T 7/0012* (2013.01);
(Continued)

(58) Field of Classification Search
CPC ........... G01N 33/4833; G01N 15/1468; G01N 33/48; G06T 7/0012; G06T 2207/30024;
(Continued)

(56) References Cited

U.S. PATENT DOCUMENTS 6,091,842 A 7/2000 Domanik et al.
6,148,096 A 11/2000 Pressman et al.
(Continued)

FOREIGN PATENT DOCUMENTS

JP 2003-521669 A 7/2003
JP 2004-170414 A 6/2004
(Continued)

OTHER PUBLICATIONS

International Search Report dated Jul. 17, 2018 issued in International Application No. PCT/JP2018/015764.
(Continued)

*Primary Examiner* — Chuong A Ngo
(74) *Attorney, Agent, or Firm* — Scully, Scott, Murphy & Presser, P.C.

(57) ABSTRACT

A specimen analysis apparatus includes: a light source; an imager configured to capture, at predetermined time intervals, images of the specimen and sequentially generate image data; a processor configured to sequentially detect the core tissue that appears in an image corresponding to the sequentially generated image data, sequentially calculate a tissue amount of the core tissue based on the sequentially detected core tissue, and determine whether the tissue amount of the core tissue is smaller than a threshold value set in advance every time the processor calculates the tissue amount; an isolator configured to isolate the core tissue from the specimen; and a drive controller configured to cause the isolator to perform the isolation operation when the tissue amount is smaller than the threshold value, and cause the isolator to stop the isolation operation when the tissue amount is equal to or larger than the threshold value.

14 Claims, 4 Drawing Sheets

(51) Int. Cl.
  *G01N 15/14* (2006.01)
  *G06T 7/00* (2017.01)
  *G06V 20/69* (2022.01)
  *G06V 10/75* (2022.01)
(52) U.S. Cl.
  CPC ............ *G06V 10/751* (2022.01); *G06V 20/69* (2022.01); *G06T 2207/30024* (2013.01); *G06V 10/56* (2022.01)
(58) Field of Classification Search
  CPC ...... G06V 10/751; G06V 20/69; G06V 10/56; G06V 2201/03; G06F 18/23213
  See application file for complete search history.

(56) References Cited

U.S. PATENT DOCUMENTS

| | | | |
|---|---|---|---|
| 6,430,309 | B1 | 8/2002 | Pressman et al. |
| 2004/0097829 | A1 | 5/2004 | McRury et al. |
| 2009/0116724 | A1 | 5/2009 | Yamashita et al. |
| 2010/0201800 | A1* | 8/2010 | Yamamoto ................ G06T 7/42 348/79 |
| 2017/0193659 | A1* | 7/2017 | Wang .................... G06T 7/0012 |

FOREIGN PATENT DOCUMENTS

| | | |
|---|---|---|
| JP | 2009-115599 A | 5/2009 |
| JP | 2013-253861 A | 12/2013 |
| JP | 2014-526035 A | 10/2014 |
| WO | 99/04244 A1 | 1/1999 |
| WO | 2012/178157 A1 | 12/2012 |

OTHER PUBLICATIONS

Iwashita, T. et al., "Macroscopic on-site quality evaluation of biopsy specimens to improve the diagnostic accuracy during EUS-guided FNA using a 19-gauge needle for solid lesions: a single-center prospective pilot study (MOSE study)", Gastrointestinal Endoscopy, vol. 81, No. 1, pp. 177-185 (2015).

* cited by examiner

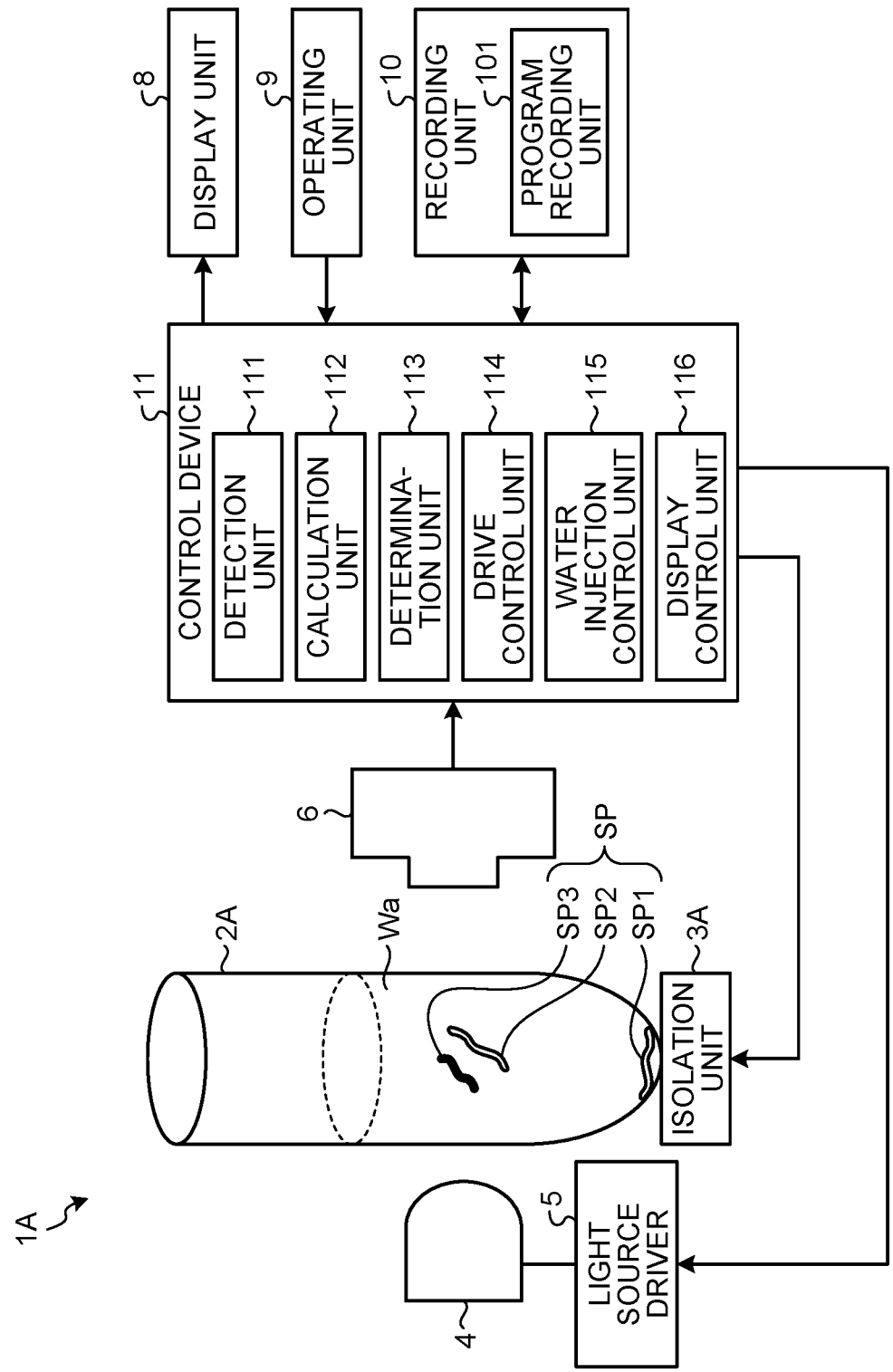

SPECIMEN ANALYSIS APPARATUS, SPECIMEN ANALYSIS METHOD, AND COMPUTER-READABLE RECORDING MEDIUM

This application is a continuation of International Application No. PCT/JP2018/015764, filed on Apr. 16, 2018, the entire contents of which are incorporated herein by reference.

BACKGROUND

The present disclosure relates to a specimen analysis apparatus, a specimen analysis method, and a computer-readable recording medium.

In intraoperative rapid cytological examination in a biopsy, in particular, in an endoscopic needle biopsy, a specimen discharged in a petri dish is usually buried in blood and clotted by being tangled with other tissue. Therefore, in Macroscopic On-Site Evaluation (MOSE) that is a process of macroscopically evaluating a biopsy specimen, a doctor loosens the clot by using tweezers or the like, isolates living tissue, that is, what is called "core tissue", of a target organ need for pathological diagnosis from other living tissue, thereafter measures an amount of the core tissue, and determines whether to obtain a specimen again based on a measurement result (for example, see Takuji Iwashita, Ichiro Yasuda, "Macroscopic on-site quality evaluation of biopsy specimens to improve the diagnostic accuracy during EUS-guided FNA using a 19-gauge needle for solid lesions: a single-center prospective pilot study (MOSE study)" GASTROINTESTINAL ENDOSCOPY, Volume 81, NO. 1, 12015, pp. 177-185

SUMMARY

According to one aspect of the present disclosure, there is provided a specimen analysis apparatus including: a light source configured to illuminate a specimen with light, the specimen containing core tissue and being accommodated in a biopsy specimen container; an imager configured to capture, at predetermined time intervals, images of the specimen that is illuminated with the light, and sequentially generate image data; a processor including hardware, the processor being configured to sequentially detect the core tissue that appears in an image corresponding to the sequentially generated image data, sequentially calculate a tissue amount of the core tissue based on the sequentially detected core tissue, and determine whether the tissue amount of the core tissue is smaller than a threshold value set in advance every time the processor calculates the tissue amount; an isolator configured to isolate the core tissue from the specimen; and a drive controller configured to cause the isolator to perform the isolation operation when the processor determines that the tissue amount is smaller than the threshold value, and cause the isolator to stop the isolation operation when the processor determines that the tissue amount is equal to or larger than the threshold value.

The above and other features, advantages and technical and industrial significance of this disclosure will be better understood by reading the following detailed description of the disclosure, when considered in connection with the accompanying drawings.

BRIEF DESCRIPTION OF THE DRAWINGS

FIG. 4 is a schematic diagram illustrating an overall configuration of a specimen analysis apparatus according to a second embodiment.

DETAILED DESCRIPTION

Hereinafter, modes for carrying out the present disclosure (hereinafter, referred to as "embodiments") will be described. In the present embodiments, a specimen analysis apparatus that isolates living tissue from a specimen obtained by a biopsy and analyzes the living tissue will be descried as an example. Further, the present disclosure is not limited by the embodiments below. Furthermore, in description of the drawings, the same components are denoted by the same reference symbols.

Figure 1:
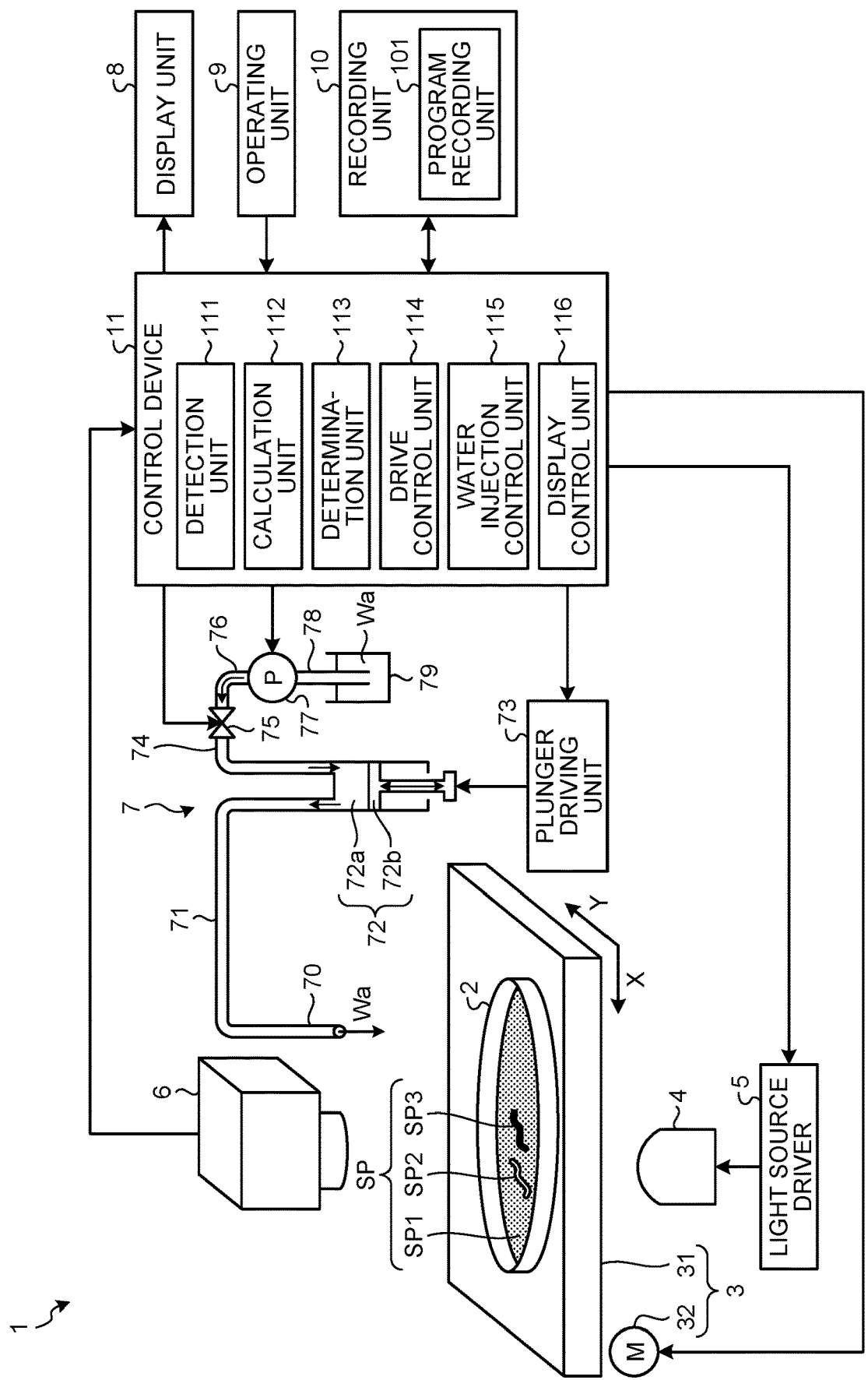
FIG. 1 is a schematic diagram illustrating an overall configuration of a specimen analysis apparatus according to a first embodiment.

FIG. 1 is a schematic diagram illustrating an overall configuration of a specimen analysis apparatus according to a first embodiment. A specimen analysis apparatus 1 illustrated in FIG. 1 isolates predetermined core tissue from a specimen SP that is accommodated in a specimen container 2, such as a petri dish, and analyzes whether a tissue amount of the isolated core tissue is equal to or larger than a threshold. The specimen analysis apparatus 1 includes an isolation unit 3, an illumination unit 4, a light source driver 5, an imaging unit 6, a water injection unit 7, a display unit 8, an operating unit 9, a recording unit 10, and a control device 11.

The specimen container 2 is placed on the isolation unit 3. The isolation unit 3 applies vibration to the specimen SP accommodated in the specimen container 2 and isolates blood SP1, core tissue SP2, and living tissue SP3 other than the core tissue SP2 from the specimen SP. The isolation unit 3 includes a stage 31 and a stage driving unit 32.

The stage 31 is arranged so as to be able to periodically move in horizontal directions (in an X direction and in a Y direction) with reference to a placement surface on which the specimen container 2 is placed. The stage 31 is configured with a transparent member, such as plastic or glass, and transmits illumination light emitted by the illumination unit 4 (to be described later). Meanwhile, the configuration of the stage 31 may appropriately be changed in accordance with a position of the illumination unit 4.

The stage driving unit 32 reciprocates the stage 31 in the horizontal directions at predetermined intervals to apply vibration to the specimen SP accommodated in the specimen container 2 under the control of the control device 11, so that the blood SP1, the core tissue SP2 and the living tissue SP3 are isolated from the specimen SP. Meanwhile, the stage driving unit 32 may cause the stage 31 to perform rotational movement to rotate about a predetermined axis or vertical movement to move up and down in a vertical direction instead of reciprocation under the control of the control device 11. It may of course be possible for the stage driving unit 32 to combine the reciprocation, the rotational movement, and the vertical movement to apply shock, such as vibration or an external force, to the specimen SP accommodated in the specimen container 2 under the control of the control device 11. The stage driving unit 32 is configured with a combination of a stepping motor, a gear, and the like.

The illumination unit 4 illuminates the specimen container 2 placed on the stage 31 with illumination light that is white light based on an electric current supplied from the light source driver 5. The illumination unit 4 is configured with a white light emitting diode (LED) lamp or a xenon lamp. The light source driver 5 supplies an electric current to the illumination unit 4 under the control of the control device 11. Meanwhile, the illumination unit 4 may use narrow-band light other than the while light so that the specimen may easily be distinguished. Specifically, the illumination unit 4 may emit LED light with an umber color in a narrow band with a peak at 600 nm, for example. In this case, contrast between blood and other tissue increases, so that the core tissue becomes more visible.

The imaging unit 6 generates image data by capturing an image of the specimen SP accommodated in the specimen container 2 and transmits the image data to the control device 11 under the control of the control device 11. The imaging unit 6 is configured with an optical system that includes at least a lens or the like for forming an object image, and an image sensor, such as a charge coupled device (CCD) or a complementary metal oxide semiconductor (CMOS).

The water injection unit 7 injects liquid Wa, such as purified water or saline, to the specimen container 2 under the control of the control device 11. The water injection unit 7 includes a water injection probe 70, a pipe 71, a syringe 72, a plunger driving unit 73, a pipe 74, an electromagnetic valve 75, a pipe 76, a water pump 77, a pipe 78, and a tank 79.

The water injection probe 70 is connected to one end of the pipe 71. The water injection probe 70 injects the liquid Wa supplied through the pipe 71 to the specimen container 2. Further, the syringe 72 is connected to the other end of the pipe 71.

The syringe 72 includes a cylinder 72a and a plunger 72b. The cylinder 72a is connected to the pipe 71 and the pipe 74, and the plunger 72b is arranged so as to be able to move back and forth inside the cylinder 72a while sliding on an inner wall surface of the cylinder 72a. The plunger driving unit 73 is configured with, for example, a linear motor. The plunger driving unit 73 causes the plunger 72b to move back and forth with respect to the cylinder 72a under the control of the control device 11.

The electromagnetic valve 75 is connected to another end of the pipe 74. The electromagnetic valve 75 performs open-close operation under the control of the control device 11. The pipe 76 is connected to another end of the electromagnetic valve 75. The water pump 77 is connected to another end of the pipe 76. The pipe 78 is connected to another end of the water pump 77. Another end of the pipe 78 is arranged inside the tank 79. The water pump 77 supplies the liquid Wa from the inside of the tank 79 under the control of the control device 11.

The water injection unit 7 configured as described above drives the water pump 77 and causes the electromagnetic valve 75 to be opened under the control of the control device 11, so that the cylinder 72a of the syringe 72 is filled with the liquid Wa supplied from the inside of the tank 79 through the pipe 78, the pipe 76, and the pipe 74. Then, the water injection unit 7 causes the electromagnetic valve 75 to be closed in a state in which the liquid Wa is fully supplied to the distal end of the water injection probe 70 from the cylinder 72a through the pipe 71 under the control of the control device 11. Thereafter, the water injection unit 7 drives the plunger driving unit 73 to move the plunger 72b under the control of the control device 11, so that the liquid Wa is injected from the water injection probe 70 to the specimen container 2.

Figure 2:
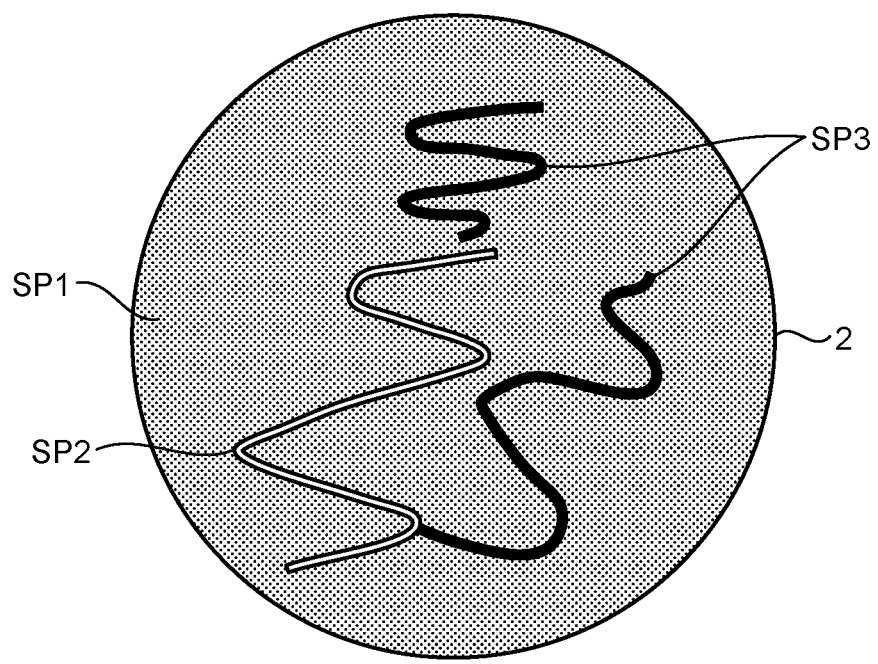
FIG. 2 is a diagram illustrating an example of an image that is displayed by a display unit of the specimen analysis apparatus according to the first embodiment.

The display unit 8 receives the image data generated by the imaging unit 6 via the control device 11, and displays an image or a live view image corresponding to the received image data. For example, as illustrated in FIG. 2, the display unit 8 displays an image corresponding to the image data that is generated by the imaging unit 6. The image P1 includes the blood SP1, the core tissue SP2, and the living tissue SP3 other than the core tissue SP2 that are isolated from the specimen SP accommodated in the specimen container 2. The display unit 8 is configured with a display panel or the like made with liquid crystal or organic electro luminescence (EL).

The operating unit 9 receives input of various kinds of operation on the specimen analysis apparatus 1, and outputs the received operation to the control device 11. The operating unit 9 is configured with a switch, a button, a touch panel, a keyboard, a mouse, and the like.

The recording unit 10 records therein various programs to be executed by the specimen analysis apparatus 1, data being processed, image data generated by the imaging unit 6, and the like. The recording unit 10 includes a program recording unit 101 that records therein various programs to be executed by the specimen analysis apparatus 1. The recording unit 10 is configured with a volatile memory, a non-volatile memory, a memory card, and the like.

The control device 11 comprehensively controls each of components of the specimen analysis apparatus 1. The control device 11 is configured with a central processing unit (CPU), a field programmable gate array (FPGA), an application specific integrated circuit (ASIC), and the like. The control device 11 includes a detection unit 111, a calculation unit 112, a determination unit 113, a drive control unit 114, a water injection control unit 115, and a display control unit 116.

The detection unit 111 detects core tissue contained in a specimen that appears in the image corresponding to the image data generated by the imaging unit 6. The detection unit 111 detects a portion of the core tissue SP2 (white earthworm) by segmentation based on the L*a*B* color space, for example. For example, the detection unit 111 detects, as the core tissue SP2 (white earthworm), a region with a luminance value that is equal to or larger than a predetermined threshold. Further, the detection unit 111 may detect the core tissue SP2 (white earthworm) from the specimen SP by color-based segmentation using k-means clustering. Meanwhile, the detection unit 111 may detect the core tissue SP2 that appears in the image corresponding to the image data generated by the imaging unit 6 based on an instruction signal that indicates a position or a region of the core tissue SP2 in the image and that is input from the operating unit 9. Furthermore, the detection unit 111 may detect the core tissue SP2 by using a classifier, which is a learning result obtained by performing learning in advance using a plurality of pieces of image data in which the core tissue SP2 (white earthworm) appears, and by using well-known template matching.

The calculation unit 112 calculates a tissue amount of the core tissue SP2 based on the core tissue SP2 detected by the detection unit 111. Specifically, the calculation unit 112 calculates at least one of a length, a width, an area, and a volume of the core tissue SP2 as the tissue amount.

The determination unit 113 determines whether the tissue amount of the core tissue SP2 calculated by the calculation unit 112 is equal to or larger than a threshold that is determined in advance. Here, the threshold is an amount that is needed for pathological diagnosis. It is of course possible to appropriately change the threshold in accordance with operation on the operating unit 9.

The drive control unit 114 drives the stage driving unit 32 to reciprocate the stage 31 based on a determination result obtained by the determination unit 113, so that the core tissue SP2 and the other living tissue SP3 are isolated from the specimen SP accommodated in the specimen container 2.

The water injection control unit 115 drives the water injection unit 7 based on the determination result obtained by the determination unit 113, to thereby inject the liquid Wa to the specimen container 2.

The display control unit 116 controls a display mode of the display unit 8. The display control unit 116 causes the display unit 8 to display a warning indicating that the tissue amount of the core tissue SP2 is smaller than the threshold based on the determination result obtained by the determination unit 113. For example, the display control unit 116 causes the display unit 8 to display a message, an icon, a graphic, or the like for requesting to perform a biopsy again. Meanwhile, while the display control unit 116 causes the display unit 8 to issue the warning, but embodiments are not limited to this example, and it may be possible to cause a speaker or the like to output the warning.

Figure 3:
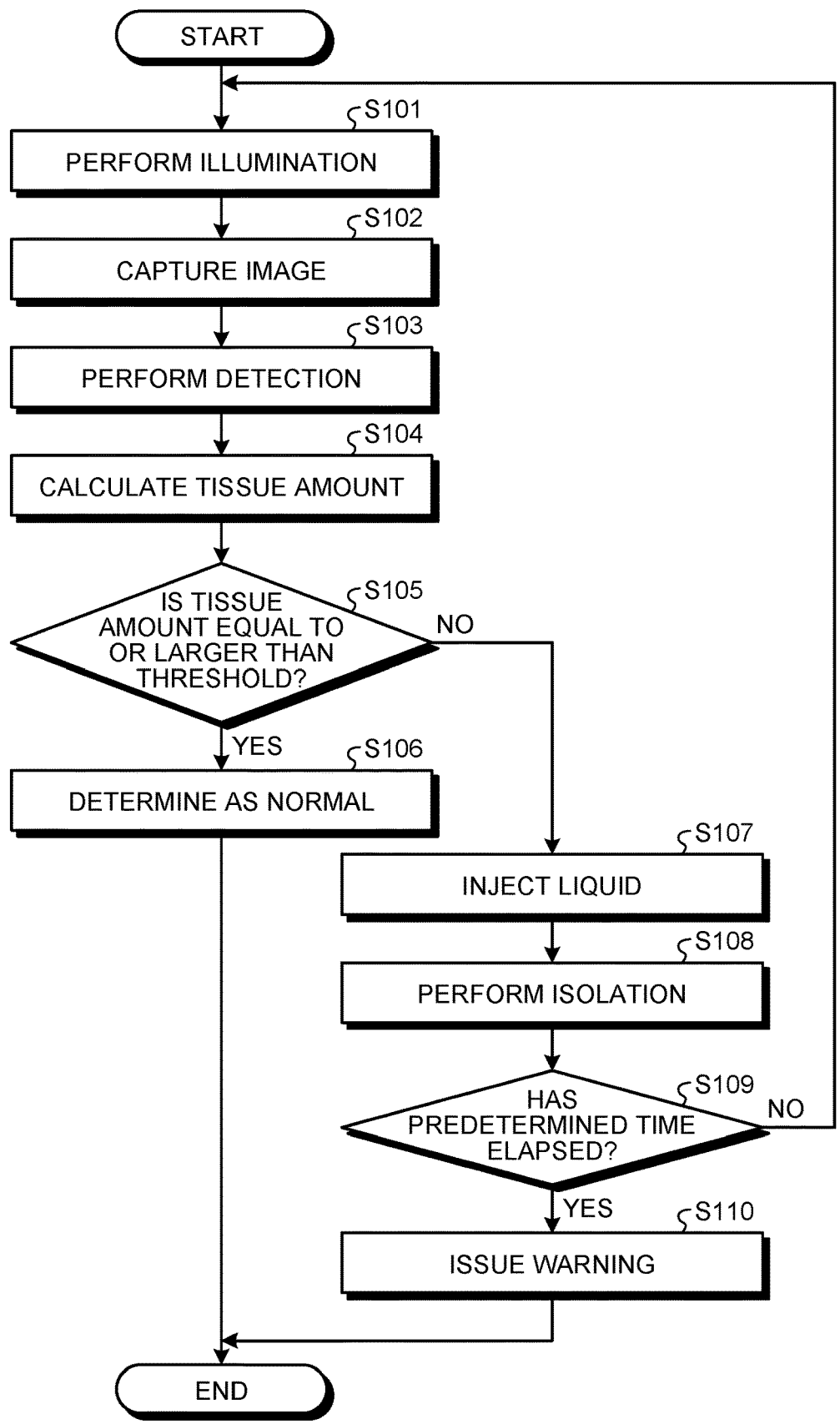
FIG. 3 is a flowchart illustrating an overview of a process performed by the specimen analysis apparatus according to the first embodiment.

A process performed by the specimen analysis apparatus 1 will be described below. FIG. 3 is a flowchart illustrating an outline of the process performed by the specimen analysis apparatus 1.

As illustrated in FIG. 3, first, the control device 11 causes the illumination unit 4 to emit illumination light by causing the light source driver 5 to supply an electric current (Step S101).

Subsequently, the imaging unit 6 captures an image of the specimen SP accommodated in the specimen container 2 and generates image data (Step S102).

Thereafter, the detection unit 111 detects the core tissue SP2 from an image corresponding to the image data generated by the imaging unit 6 (Step S103).

Subsequently, the calculation unit 112 calculates a tissue amount of the core tissue SP2 detected by the detection unit 111 (Step S104).

Thereafter, the determination unit 113 determines whether the tissue amount of the core tissue SP2 calculated by the calculation unit 112 is equal to or larger than the threshold (Step S105). If the determination unit 113 determines that the tissue amount of the core tissue SP2 calculated by the calculation unit 112 is equal to or larger than the threshold (Step S105: Yes), the specimen analysis apparatus 1 proceeds to Step S106 to be described later. In contrast, if the determination unit 113 determines that the tissue amount of the core tissue SP2 calculated by the calculation unit 112 is not equal to or larger than the threshold (Step S105: No), the specimen analysis apparatus 1 proceeds to Step S107 to be described later.

At Step S106, the display control unit 116 causes the display unit 8 to display information indicating that the tissue amount of the core tissue SP2 is normal. After Step S106, the specimen analysis apparatus 1 terminates the process.

At Step S107, the water injection control unit 115 drives the water injection unit 7 to inject the liquid Wa to the specimen container 2.

Subsequently, the drive control unit 114 drives the isolation unit 3 to apply vibration to the specimen container 2, to thereby isolate the core tissue SP2 from the specimen SP (Step S108).

Thereafter, the determination unit 113 determines whether a predetermined time has elapsed since the placement of the specimen container 2 on the isolation unit 3 (Step S109). If the determination unit 113 determines that the predetermined time has elapsed since the placement of the specimen container 2 on the isolation unit 3 (Step S109: Yes), the specimen analysis apparatus 1 proceeds to Step S110 to be described later. In contrast, if the determination unit 113 determines that the predetermined time has not elapsed since the placement of the specimen container 2 on the isolation unit 3 (Step S109: No), the specimen analysis apparatus 1 returns to Step S101 described above.

At Step S110, the display control unit 116 causes the display unit 8 to display a warning indicating that the tissue amount of the core tissue SP2 is abnormal. After Step S110, the specimen analysis apparatus 1 terminates the process.

According to the first embodiment as described above, the drive control unit 114 controls isolation operation performed by the isolation unit 3, based on the tissue amount of the core tissue SP2 calculated by the calculation unit 112, so that it is possible to analyze whether the tissue amount of the core tissue needed for pathological diagnosis is ensured through simple operation.

Furthermore, according to the first embodiment, if the determination unit 113 determines that the tissue amount of the core tissue SP2 is smaller than the threshold, the drive control unit 114 causes the isolation unit 3 to perform the isolation operation, and, if the determination unit 113 determines that the tissue amount of the core tissue SP2 is equal to or larger than the threshold, the drive control unit 114 causes the isolation unit 3 to stop the isolation operation, so that it is possible to analyze whether the tissue amount of the core tissue SP2 needed for pathological diagnosis is ensured.

Moreover, according to the first embodiment, if the determination unit 113 determines that the tissue amount of the core tissue SP2 is smaller than the threshold after a lapse of a predetermined time, the drive control unit 114 causes the isolation unit 3 to stop the isolation operation, so that it is possible to omit unnecessary operation.

Furthermore, according to the first embodiment, if the determination unit 113 determines that the tissue amount of the core tissue SP2 is smaller than the threshold after a lapse of a predetermined time, the display control unit 116 causes the display unit 8 to display a warning indicating that the specimen is abnormal, so that a user is able to intuitively recognize that the tissue amount of the core tissue SP2 needed for pathological diagnosis is not ensured.

Moreover, according to the first embodiment, the water injection control unit 115 controls injection of the liquid Wa performed by the water injection unit 7 based on the determination result obtained by the determination unit 113, so that it is possible to loosen a clot of the specimen SP in the specimen container 2.

Meanwhile, in the first embodiment, the core tissue SP2 is isolated from the specimen SP by applying vibration to the specimen SP in the specimen container 2 on the isolation unit 3, but embodiments are not limited to this example, and it may be possible to isolate the core tissue SP2 from the specimen by, for example, ultrasonic waves.

Furthermore, in the first embodiment, whether the tissue amount of the core tissue SP2 is smaller than the threshold is determined again after a lapse of a predetermined time since the determination on the tissue amount of the core tissue SP2 performed by the determination unit 113, but embodiments are not limited to this example, and it may be possible to determine an amount of increase in the tissue amount of the core tissue SP2 calculated by the calculation unit 112 is smaller than a threshold that is set in advance, for example. In this case, if the determination unit 113 determines that the amount of increase in the tissue amount of the core tissue SP2 is equal to or larger than the threshold, the drive control unit 114 causes the isolation unit 3 to perform the isolation operation, and, if the determination unit 113 determines that the amount of increase in the tissue amount of the core tissue SP2 is smaller than the threshold, the drive control unit 114 causes the isolation unit 3 to stop the isolation operation. With this configuration, it is possible to control the isolation operation performed by the isolation unit 3 in accordance with an isolation state of the core tissue SP2 from the specimen SP, so that it is possible to omit unnecessary operation.

A second embodiment will be described below. The second embodiment has a different configuration from the configuration of the first embodiment as described above. Specifically, in the second embodiment, a mechanism that injects liquid is not included. In the following, a configuration of a specimen analysis apparatus according to the second embodiment will be described. Meanwhile, the same components as those of the specimen analysis apparatus 1 according to the first embodiment as described above will be denoted by the same reference symbols, and explanation of the components will be omitted.

FIG. 4 is a schematic diagram illustrating an overall configuration of the specimen analysis apparatus according to the second embodiment. A specimen analysis apparatus 1A illustrated in FIG. 4 includes components that are different from those of the specimen container 2 and the isolation unit 3 included in the specimen analysis apparatus 1, and does not include the water injection unit 7. Specifically, as illustrated in FIG. 4, the specimen analysis apparatus 1A analyzes the tissue amount of the core tissue SP2 with respect to the specimen SP accommodated in a specimen container 2A.

The specimen container 2A is configured with a bottomed test tube, a flask, a micro tube, or the like. The liquid Wa, such as saline, is contained in advance in the specimen container 2A. In this state, the specimen SP for which a biopsy has been performed by a doctor or the like is discharged from a puncture needle.

An isolation unit 3A causes the specimen container 2A whose bottom portion comes into contact with the isolation unit 3A to whirl at high speed under the control of the control device 11, to thereby generate a whirlpool inside the specimen container 2A and stir the liquid Wa containing the specimen SP inside the specimen container 2A with the aid of the whirlpool. Accordingly, the blood SP1, the core tissue SP2, and the living tissue SP3 are isolated from the specimen SP accommodated in the specimen container 2A. The isolation unit 3A is configured with, for example, a vortex mixer or the like. Meanwhile, in the second embodiment, it may be possible to use a magnetic stirrer, an ultrasonic device, or the like as long as it is possible to stir the liquid Wa containing the specimen SP in the specimen container 2A, for example.

The specimen analysis apparatus 1A configured as described above performs the same process as the process performed by the specimen analysis apparatus 1 according to the first embodiment as described above, and therefore, detailed explanation of the process will be omitted.

According to the second embodiment as described above, it is possible to analyze whether the tissue amount of the core tissue SP2 needed for pathological diagnosis is ensured through simple operation.

Variations may be made by appropriately combining a plurality of constituent elements disclosed in the first and the second embodiments as described above. For example, some constituent elements may be deleted from all of the constituent elements described in the first and the second embodiments as described above. Furthermore, the constituent elements described in the first and the second embodiments may be appropriately combined.

Moreover, in the first and the second embodiments, the control unit and the illumination unit are separated from each other, but they may be integrated together.

Furthermore, in the first and the second embodiments, a "unit" described above may be replaced with a "means" or a "circuit". For example, the control unit may be replaced with a control means or a control circuit.

Moreover, a program to be executed by the specimen analysis apparatus according to the present disclosure is provided by being recorded in a computer-readable recording medium, such as a compact disc-ROM (CD-ROM), a flexible disk (FD), CD-recordable (CD-R), a digital versatile disk (DVD), a universal serial bus (USB) medium, or a flash memory, in a computer-installable or a computer-executable file data format.

Furthermore, the program to be executed by the specimen analysis apparatus according to the present disclosure may be configured such that the program is stored in a computer connected to a network, such as the Internet, and provided by download via the network. Moreover, the program to be executed by the specimen analysis apparatus according to the present disclosure may be configured such that the program is provided or distributed via a network, such as the Internet.

In describing the flowchart in the present specification, context of the processes among the steps is disclosed by using expressions such as "first", "thereafter", and "subsequently", but the sequences of the processes necessary for carrying out the present disclosure are not uniquely defined by these expressions. In other words, the sequences of the processes in the flowchart described in the present specification may be modified as long as there is no contradiction.

While some embodiments have been explained in detail above based on the drawings, the embodiments are described by way of example, and the present disclosure may be embodied in various other forms with various changes or modifications based on knowledge of a person skilled in the art, in addition to the embodiments described in the present specification.

According to the present disclosure, it is possible to analyze whether a tissue amount of core tissue needed for pathological diagnosis is ensured by performing simple operation on biopsy specimen tissue, and allow even a less-experienced doctor to accurately perform the MOSE process.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:
1. A specimen analysis apparatus comprising:
a light source configured to illuminate a specimen with light, the specimen containing core tissue and being accommodated in a biopsy specimen container;
an imager configured to capture, at predetermined time intervals, images of the specimen that is illuminated with the light, and sequentially generate image data;

a processor comprising hardware, the processor being configured to
sequentially detect the core tissue that appears in an image corresponding to the sequentially generated image data,
sequentially calculate a tissue amount of the core tissue based on the sequentially detected core tissue, and
determine whether the tissue amount of the core tissue is smaller than a threshold value set in advance every time the processor calculates the tissue amount;
an isolator configured to isolate the core tissue from the specimen; and
a drive controller configured to
cause the isolator to perform the isolation operation when the processor determines that the tissue amount is smaller than the threshold value, and
cause the isolator to stop the isolation operation when the processor determines that the tissue amount is equal to or larger than the threshold value.

2. The specimen analysis apparatus according to claim 1, wherein
the processor is configured to determine whether the tissue amount is smaller than the threshold value after a lapse of a predetermined time since determination on the tissue amount, and
the drive controller is configured to cause the isolator to stop the isolation operation when the processor determines that the tissue amount is smaller than the threshold value after the lapse of the predetermined time.

3. The specimen analysis apparatus according to claim 2, further comprising:
a display panel configured to display an image corresponding to the image data; and
a display controller configured to control a display mode of the display panel, wherein
the display controller is configured to cause the display panel to display a warning indicating that the specimen is abnormal when the processor determines that the tissue amount is smaller than the threshold value.

4. The specimen analysis apparatus according to claim 1, further comprising:
a water injector configured to inject liquid to the biopsy specimen container.

5. The specimen analysis apparatus according to claim 4, further comprising;
a water injector controller configured to control injection of the liquid performed by the water injector, based on a determination result obtained by the processor.

6. The specimen analysis apparatus according to claim 1, wherein the isolator is configured to isolate the core tissue from the specimen by applying vibration to the specimen.

7. The specimen analysis apparatus according to claim 1, wherein the isolator is configured to isolate the core tissue from the specimen by stirring the liquid in the biopsy specimen container.

8. A specimen analysis apparatus comprising:
a light source configured to illuminate a specimen with light, the specimen containing core tissue and being accommodated in a biopsy specimen container;
an imager configured to capture an image of the specimen that is illuminated with the light by the light source, and generate image data;
a processor comprising hardware, the processor being configured to
detect the core tissue that appears in an image corresponding to the generated image data,
calculate a tissue amount of the core tissue based on the detected core tissue,
determine whether an amount of increase in the tissue amount of the calculated core tissue is smaller than a threshold value that is set in advance;
an isolator configured to isolate the core tissue from the specimen; and
a drive controller configured to
cause the isolator to perform isolation operation when the processor determines that the amount of increase in the tissue amount is equal to or larger than the threshold value, and
cause the isolator to stop the isolation operation when the processor determines that the amount of increase in the tissue amount is smaller than the threshold value.

9. The specimen analysis apparatus according to claim 8, further comprising:
a water injector configured to inject liquid to the biopsy specimen container.

10. The specimen analysis apparatus according to claim 9, further comprising;
a water injector controller configured to control injection of the liquid performed by the water injector, based on a determination result obtained by the processor.

11. The specimen analysis apparatus according to claim 8, wherein the isolator is configured to isolate the core tissue from the specimen by applying vibration to the specimen.

12. The specimen analysis apparatus according to claim 8, wherein the isolator is configured to isolate the core tissue from the specimen by stirring the liquid in the biopsy specimen container.

13. A specimen analysis method comprising:
illuminating a specimen with light, the specimen containing core tissue and being accommodated in a biopsy specimen container;
capturing, at predetermined time intervals, images of the specimen that is illuminated with the light, and sequentially generating image data;
sequentially detecting the core tissue that appears in an image corresponding to the sequentially generated image data,
sequentially calculating a tissue amount of the core tissue based on the sequentially detected core tissue, and
determining whether the tissue amount of the core tissue is smaller than a threshold value set in advance every time the tissue amount is calculated;
performing isolation of the core tissue from the specimen when the tissue amount is determined to be smaller than the threshold value, and
stopping stop the isolation when the tissue amount is determined to be equal to or larger than the threshold value.

14. A non-transitory computer-readable recording medium on which an executable program is recorded, the program causing a processor of a computer to execute:
illuminating a specimen with light, the specimen containing core tissue and being accommodated in a biopsy specimen container;
capturing, at predetermined time intervals, images of the specimen that is illuminated with the light, and sequentially generating image data;
sequentially detecting the core tissue that appears in an image corresponding to the sequentially generated image data,
sequentially calculating a tissue amount of the core tissue based on the sequentially detected core tissue, and determining whether the tissue amount of the core tissue is smaller than a threshold value set in advance every time the tissue amount is calculated;

performing isolation of the core tissue from the specimen when the tissue amount is determined to be smaller than the threshold value, and stopping stop the isolation when the tissue amount is determined to be equal to or larger than the threshold value.

* * * * *